(12) United States Patent
Bombardelli et al.

(10) Patent No.: US 7,582,639 B2
(45) Date of Patent: Sep. 1, 2009

(54) N-DEACETYLTHIOCOLCHICINE DERIVATIVES, THEIR USE AND PHARMACEUTICAL FORMULATIONS CONTAINING THEM

(75) Inventors: Ezio Bombardelli, Groppello Cairoli (IT); Gabriele Fontana, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/142,502

(22) Filed: Jun. 19, 2008

(65) Prior Publication Data

US 2008/0255151 A1 Oct. 16, 2008

Related U.S. Application Data

(62) Division of application No. 10/588,012, filed as application No. PCT/EP2005/000987 on Feb. 1, 2005, now Pat. No. 7,399,788.

(30) Foreign Application Priority Data

Feb. 3, 2004 (IT) .......................... MI2004A0164

(51) Int. Cl.
*A61K 31/4965* (2006.01)
*C07D 241/04* (2006.01)
*C07D 295/00* (2006.01)
(52) U.S. Cl. .................. 514/255.01; 544/380
(58) Field of Classification Search ............ 514/255.01; 544/380
See application file for complete search history.

(56) References Cited

U.S. PATENT DOCUMENTS

| 3,090,729 A | 5/1963 | Bellet et al. |
| 2004/0204370 A1 | 10/2004 | Yang |

FOREIGN PATENT DOCUMENTS

| WO | 01/68597 | 9/2001 |
| WO | WO 01/68597 | * 9/2001 |

\* cited by examiner

*Primary Examiner*—James O Wilson
*Assistant Examiner*—Erich A Leeser
(74) *Attorney, Agent, or Firm*—Young & Thompson

(57) ABSTRACT

Disclosed is a series of N-deacetylthiocolchicine derivatives of formula I

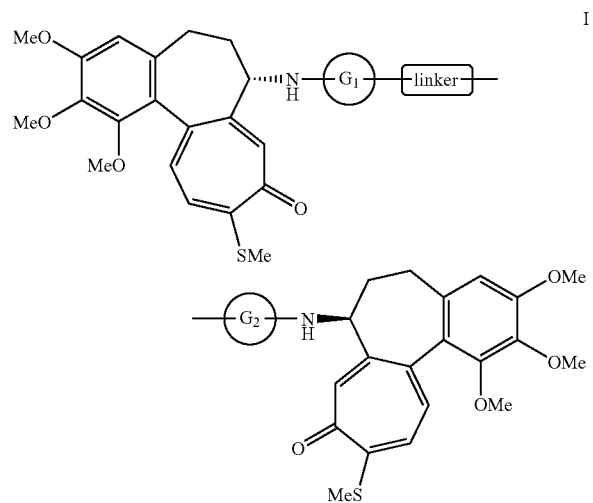

in which:
the linker is a bivalent straight or branched $C_1$-$C_8$ alkyl residue, $C_3$-$C_8$ cycloalkyl, a phenylene or heterocyclic $C_4$-$C_6$ ring;
the $G_1$ and $G_2$ junctions, which can be the same or different, are —CO—, —CONH—, —$CR_2$— groups in which $R_2$ is hydrogen or a straight $C_1$-$C_4$ alkyl residue,
or the $G_1$-linker-$G_2$ group is the —CO— group.

The compounds of formula I have antiproliferative, antiinflammatory, antiarthritic and antiviral activity.

2 Claims, No Drawings

N-DEACETYLTHIOCOLCHICINE DERIVATIVES, THEIR USE AND PHARMACEUTICAL FORMULATIONS CONTAINING THEM

This application is a division of application Ser. No. 10/588,012, filed on Oct. 6, 2006, the entire contents of which are hereby incorporated by reference.

DISCLOSURE OF THE INVENTION

The present invention relates to N-deacetylthiocolchicine derivatives of formula I

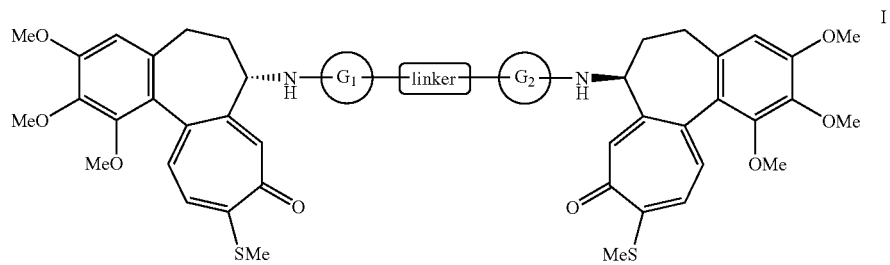

in which:
the linker is a bivalent straight or branched $C_1$-$C_8$ alkyl residue, $C_3$-$C_8$ cycloalkyl, a phenylene or $C_4$-$C_6$ heterocyclic ring;
the $G_1$ and $G_2$, junctions which can be the same or different, are —CO—, —CONH—, —$CR_2$— groups, in which $R_2$ is hydrogen or a straight $C_1$-$C_4$ alkyl residue, or the $G_1$-linker-$G_2$ group is the —CO— group.
The compounds of formula I have antiproliferative, antiinflammatory, antiarthritic and antiviral activity.

BACKGROUND OF THE INVENTION

Colchicine and thiocolchicine have been known for some time in the medical practice. Colchicine is used in the therapy of gout and related inflammatories states. 3-O-Demethylthiocolchicine glucoside is used as miorelaxant in spasticity and muscle pains due to contractures. However, in both cases the use of these compounds is limited due to their high toxicity.

Colchicine and thiocolchicine are also known antiblastic compounds, ie compounds that are able to destabilize the microtubules through interaction with tubuline. The possible use of a number of colchicine- and thiocolchicine-derivatives as antitumor medicaments has been studied. Due to their low therapeutic index none of them has been successful, with the sole exception of demecolchicine, introduced in therapy in the sixties for the treatment of leukemic forms and subsequently replaced by the more effective Vinca alkaloids.

WO 01/6895597 discloses thiocolchicine dimers in which the thiocolchicine residues are liked through a linear aliphatic amido or amido-ureido bridge.

DISCLOSURE OF THE INVENTION

It has now been found that the compounds of formula I have antiproliferative activity higher than colchicine and thiocolchicine, in particular on cells expressing the MDR (Multi-Drug Resistance) phenotype.

The compounds of the invention are also more advantageous than the dimers disclosed in WO 01/68597. Moreover, it has been found that the introduction of an aromatic basic residue in the linker increases of a dimension order the cytotoxicity of the compounds. The introduction of linkers able to properly orient the thiocolchicine residues in the space amplifies the spectrum of activity spectrum on resistant tumours. The cytotoxicity of the compounds of formula I proved comparable to that of the most effective antitumour medicaments, whereas the action spectrum is remarkably wider on resistant tumours.

DETAILED DISCLOSURE OF THE INVENTION

Disclosed are N-deacetylthiocolchicine derivatives of formula

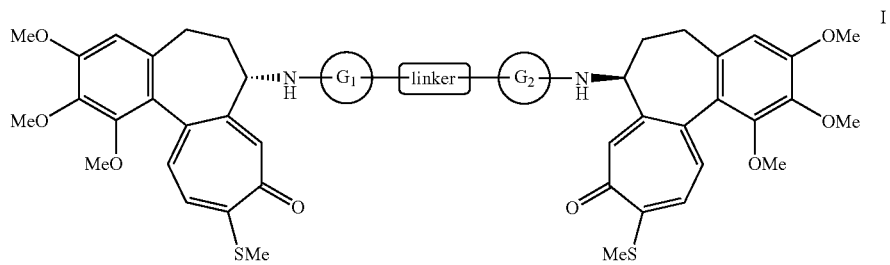

in which:
the linker is a bivalent straight or branched $C_1$-$C_8$ alkyl residue, $C_3$-$C_8$ cycloalkyl, a phenylene or a $C_4$-$C_6$ heterocyclic ring;
the $G_1$ and $G_2$ junctions, which can be the same or different, are —CO—, —CONH—, —$CR_2$— groups, wherein $R_2$ is hydrogen or a straight $C_1$-$C_4$ alkyl residue,
or the $G_1$-linker-$G_2$ group is the —CO— group
with the proviso that, when $G_1$ and $G_2$ are both CO, or when $G_1$ is —CONH— and $G_2$ is —CO— the linker is different from an alkyl residue.

Examples of alkyl bivalent residues comprise straight residues with two, three, four, five or six carbon atoms.

Examples of cycloalkyl groups comprise 1,3-cyclohexylene and 1,4-cyclohexylene.

Examples of phenylene groups comprise 1,2-, 1,3- or 1,4-phenylene.

Examples of heterocyclic groups comprise pyridyl, pyrazinyl, pyrimidinyl, piperidinyl, piperazinyl linked to the $G_1$ and $G_2$ groups through two carbon atoms of the ring, for example in the positions 3,5 or 2,5 or 2,6.

$G_1$ and $G_2$ are preferably both CO or CONH.

The linker is preferably a phenylene, cycloalkylene or heterocyclic group as defined above, preferably a heterocyclic group comprising at least one basic nitrogen (pyridyl, pyrimidinyl, pyrazinyl, piperidinyl).

The formulas of some specific compounds of formula I are reported hereinbelow:

TABLE 1

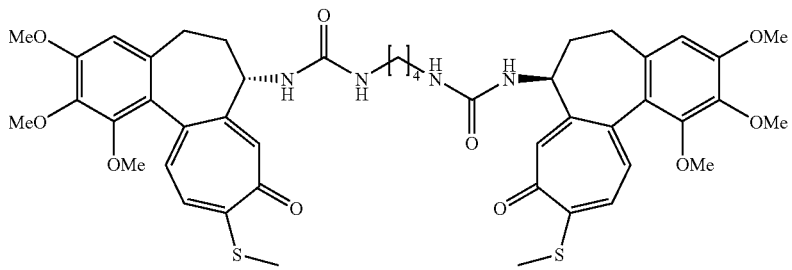

FW = 886
C46H54N4O10S2

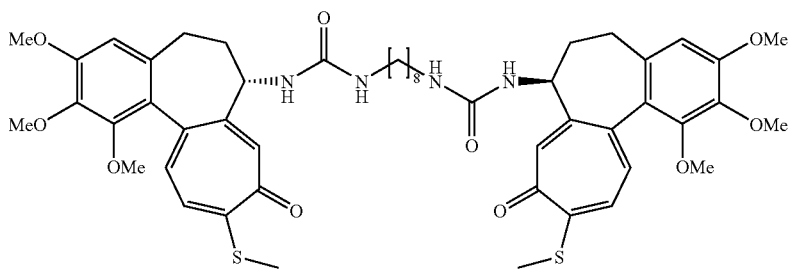

FW = 942
C50H62N4O10S2

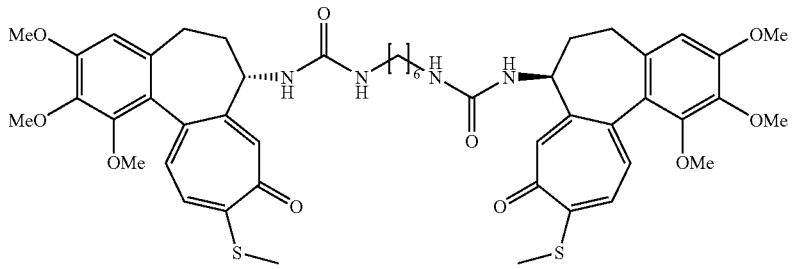

FW = 914
C48H58N4O10S2

TABLE 1-continued
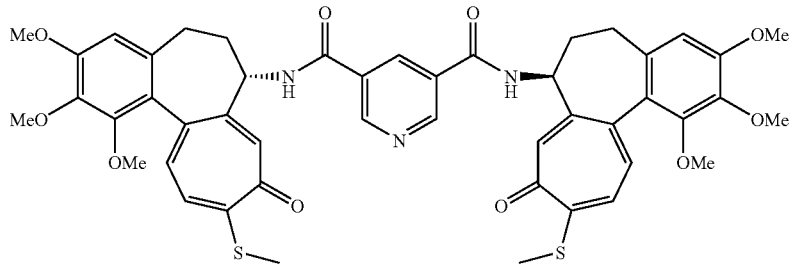
FW = 877
C47H47N3O10S2
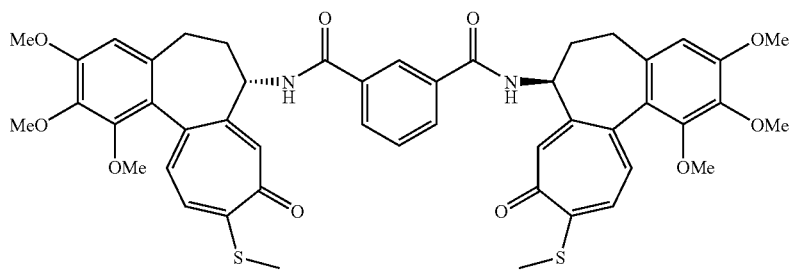
FW = 876
C48H48N2O10S2
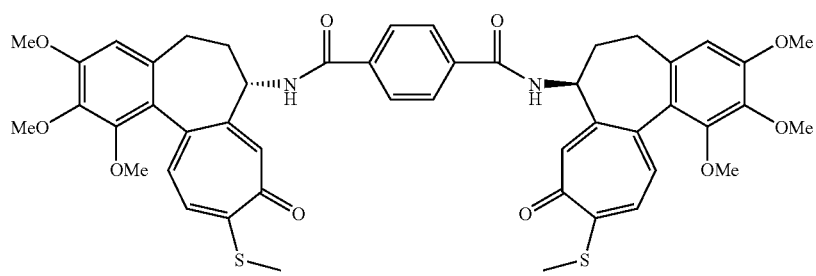
FW = 876
C48H48N2O10S2
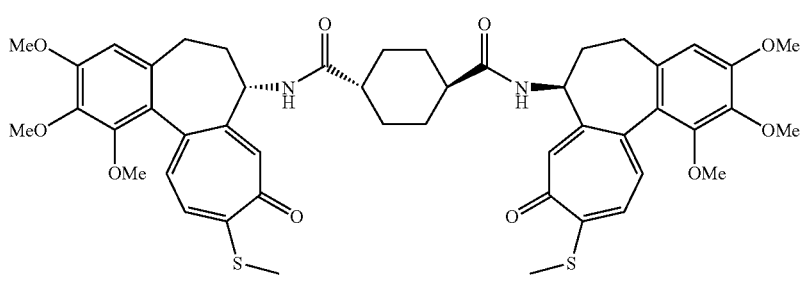
FW = 882
C48H54N2O10S2
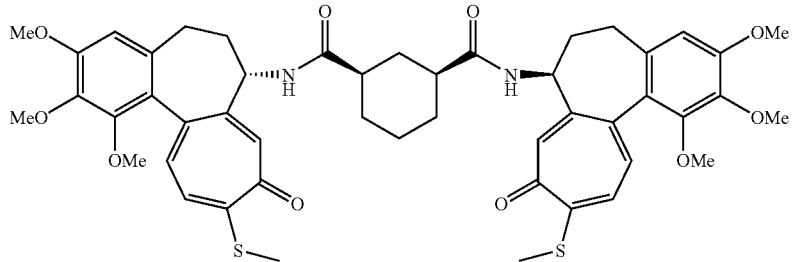
FW = 882
C48H54N2O10S2

TABLE 1-continued
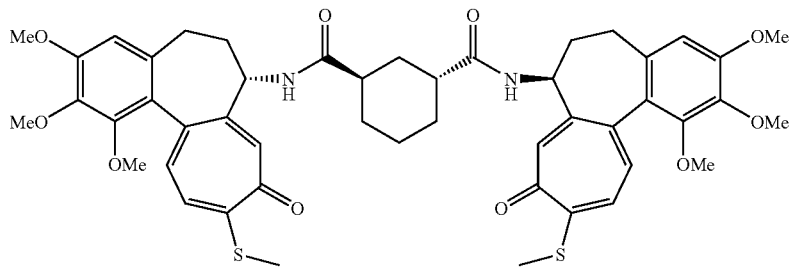
FW = 882
C48H54N2O10S2
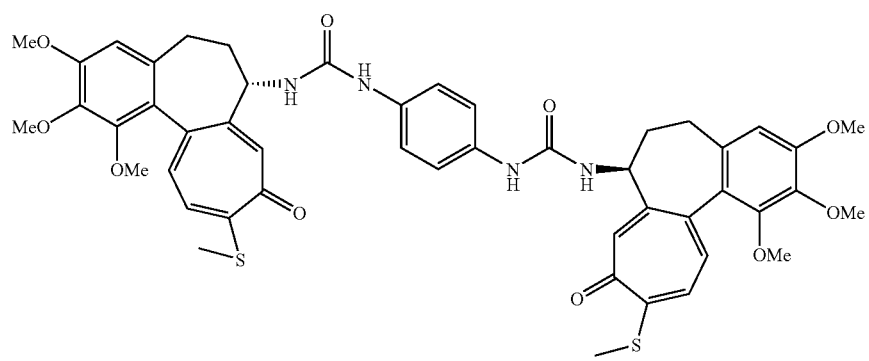
FW = 906
C48H50N4O10S2
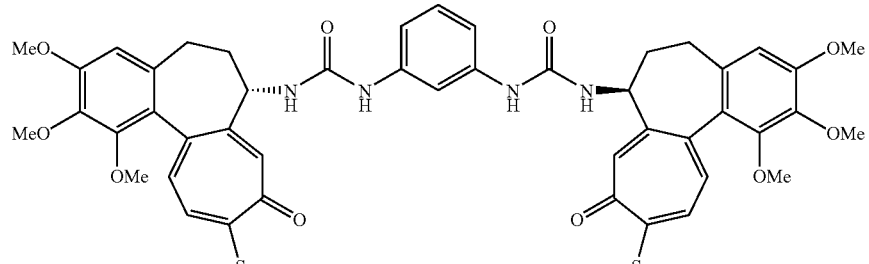
FW = 906
C48H50N4O10S2
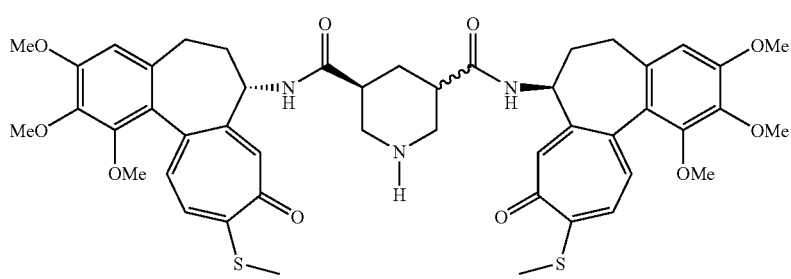
FW = 883
C47H53N3O10S2

TABLE 1-continued

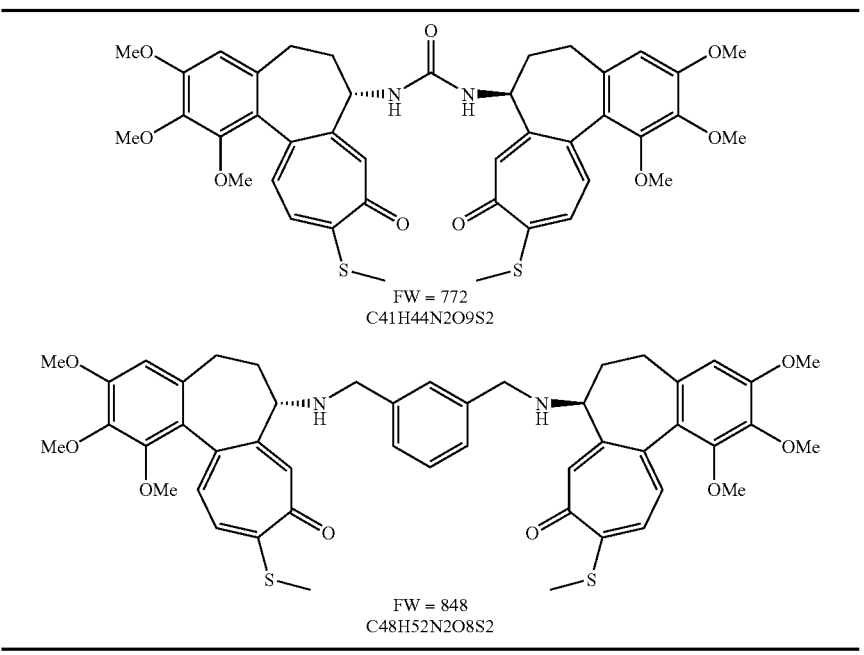

The compounds of formula I have antiproliferative, antiinflammatory, antiarthritic and antiviral activity.

The compounds of the present invention are prepared as described in the following.

The compounds of the invention of formula I in which $G_1=G_2=CO$ (bis-amides) are prepared by reacting N-deacetylthiocolchicine with activated derivatives of the desired dicarboxylic acids in inert solvents. Among activated dicarboxylic acids derivatives, particularly preferred are acid chlorides and mixed anhydrides, particularly with trifluoroacetic acid. Among inert solvents, particularly preferred are chlorinated solvents. As an alternative, N-deacetylthiocolchicine is reacted with the desired dicarboxylic acid in the presence of DMAP (4-N,N-dimethylaminopyridine) and a condensing agent, DCC (dicyclohexylcarbodiimide), at room temperature, or under heating, and with vigorous stirring until disappearance of the starting products.

The compounds of the invention of formula I in which $G_1=G_2=CONH$ (bis-ureas) are prepared by reacting N-deacetylthiocolchicine with the desired bis-isocyanate in an inert solvent. When the selected isocyanate is not commercially available, it is generated in situ by Lossen rearrangement of the corresponding hydroxamic acid by treatment with a carbodiimide and a base. Alternatively, the isocyanate is generated by treatment of the corresponding amide with lead tetraacetate.

The compounds in which $G_1$ and $G_2$ are a —$CR_2$— group (bis-amines) are prepared by reductive amination of N-deacetylthiocolchicine with suitable dialdehydes. Alternatively, the bis-amines are obtained by alkylation of the thiocolchicine nitrogen with suitable halogen- or tosyl-derivatives. In rare cases the bis-amines are prepared from the corresponding bis-amides through reduction with boranes.

The compounds with different $G_1$ and $G_2$ are prepared in two steps through a combination of the methods cited above.

The activity of the compounds of formula I was evaluated on a large number of tumour cells expressing different resistance. The most interesting activity has been observed in ovary, colon, liver and pancreas tumour lines.

Table 2 reports $IC_{50}$ values (expressed in nanomols) of some compounds of the invention in comparison with the dimer disclosed in example 3 of WO 001/68597.

TABLE 2

$IC_{50}{}^1$ (expressed in nMoles) of thiocolchicine dimers after 72 hours

| Compounds | $IC_{50}$ (nM) ± S.E. | | | | | | |
|---|---|---|---|---|---|---|---|
| | MCF7 (breast) | MCF7-R (MDR+) | A2780 (Ovarian) | A2780/ dx (Pgp+) | A2780/ top (resistant to topotecan) | A2780/ pt (resistant to tocisplatin) | Widr (colon) |
| E.g. 3 of WO 001/68597 | 7.9 ± 0.5 | 33 ± 2.8 | 238 ± 74 | 697 ± 192 | 288 ± 13 | 252 ± 0.7 | 351 ± 4 |

TABLE 2-continued

| | IC$_{50}$[1] (expressed in nMoles) of thiocolchicine dimers after 72 hours | | | | | | |
|---|---|---|---|---|---|---|---|
| | IC$_{50}$ (nM) ± S.E. | | | | | | |
| Compounds | MCF7 (breast) | MCF7-R (MDR+) | A2780 (Ovarian) | A2780/ dx (Pgp+) | A2780/ top (resistant to topotecan) | A2780/ pt (resistant to tocisplatin) | Widr (colon) |
| E.g. 1 | 0.7 ± 0.1 | 72 ± 4.3 | 3 ± 0.4 | 806 ± 286 | 6.9 ± 4.2 | 3.7 ± 0.6 | 25 ± 26.4 |
| E.g. 3 | 1.5 ± 0.1 | 108 ± 14 | 8 ± 5.6 | 922 ± 164 | 5.5 ± 0.1 | 23 ± 4.6 | 48 ± 24 |
| E.g. 2 | 14 ± 0.9 | 135 ± 11 | 37 ± 5 | 1273 ± 382 | 32 ± 24 | 26 ± 1.0 | 230 ± 166 |
| E.g. 4 | | | 252 ± 38 | 3841 ± 224 | 152 ± 36 | 331 ± 63 | 650 ± 40 |

[1]IC$_{50}$: concentration that inhibits cell growth by 50% compared with non treated cells.

Cytotoxic activity was evaluated according to the procedure described by M. C. Alley et al., *Cancer Research* 1998, 48, 589-601.

All the thiocolchicine dimers with the claimed spacers proved to possess antiproliferative, antiinflammatory and antiviral activity. These compounds are therefore useful in the treatment of neoplasias of various origin, deforming rheumatoid arthritis and in the treatment of the Kaposi tumour whose retroviral component is ascertained. The inhibiting action of viral replication combined with the inhibition of cell proliferation in actively proliferating tissues is of particular interest, considering the origin of several human tumours.

For this purpose, the compounds of the invention will be administered as pharmaceutical compositions suitable for intravenous, parenteral, oral, transdermal administration. A particularly useful aspect of the invention relates to the preparation of complexes with plasma proteins, in particular engineered human albumin. The protein complexes of these derivatives are obtained adding to a concentrated solution of albumin the compound dissolved in dioxane in a time that allows the reaction between the involved molecular species. After reacting the two molecular species (albumin and the colchicine derivative) under physiological pH and ionic strength conditions, the resulting solution is lyophilised. If the lyophilised solution is prepared under conditions of absolute sterility, it is ready for endovenous injection; the lyophilised solution, after dispersion in suitable and compatible excipients, can be compressed and administered through the oral route providing plasma concentrations of medicaments close to those obtainable though the parenteral route. As an alternative to the use of plasma proteins, given the poor water solubility of the compounds, variously functionalised cyclodextrins or acryl matrices suitable for parenteral administration in manhumans can be advantageously used.

Depending on the administration route, the dosage of the compounds will range from 1 to 20 mg/m$^2$ body area. The preferred administration routes are locoregional injection, intravenous and oral administration.

Examples of compositions comprise freeze-dried vials, supported lyophilised tablets and drinkable solutions. Any other agents that dissolve the compounds with to an acceptable extent for administration, such as Tween, Cremophor and suitable mixtures thereof with PEG or alcohols are also comprised in the present invention.

The following examples illustrate the invention in greater detail.

EXAMPLES

Example 1

3,5-Pyridinedicarboxylic acid bis-(N-deacetylthiocolchicine)amide 10 g of N-deacetylthiocolchicine are dissolved in 60 ml of methylene chloride. 2.24 g (0.5 eq) of 3,5-pyridinecarboxylic acid, 1.64 g (0.5 eq) of N,N-dimethylaminopyridine (DMAP) and 8.3 g (1.5 eq) of dicyclohexylcarbodiimide (DCC) are then added with under vigorous stirring. The mixture is left under stirring, monitoring the reaction by TLC (AcOEt: MeOH 10:1), until disappearance of the reagents (about 12 hours). The solution is then filtered through Celite, washing the pad with methylene chloride (2×100 ml). The combined organic phases are washed first with an same equal volume of 1N HCl and then with 1N NaOH. The organic phase is dried over sodium sulfate and evaporated under vacuum. The residue is purified by filtration on silica gel (AcOEt:MeOH 10:1). The resulting product is dried overnight in a static dryer at 40° C. under vacuum to give 7.5 g of final product.

$^1$HNMR (300 MHz, CDCl$_3$): 1.00-1.42 (m, 2H), 1.50-2.00 (m, 2H), 2.05-2.30 (m, 2H), 2.30-2.50 (m, 2H), 2.52 (s, 3H, SMe), 3.71 (s, 3H, MeO-1), 3.90 (s, 3H, MeO-2), 3.96 (s, 3H, MeO-3), 4.80-4.92 (m, 2H, H-7), 6.47 (s, 2H, H-8), 7.18 (d, 12.0 Hz, 2H, H-12), 7.38 (d, 12.0 Hz, 2H, H-11), 7.67 (s, 2H, H-4), 8.52 (br s, 2H, NH), 9.28 (s, 2H, H-2'+H-6' ), 9.60 (s, 1H, H-4');

$^{13}$CNMR (75 MHz, CDCl$_3$): 182.64, 164.25, 158.88, 154.12, 152.59, 152.34, 151.33, 141.92, 139.33, 135.48, 134.47, 132.74, 129.04, 128.54, 127.48, 125.71, 107.74, 61.88, 61.61, 56.49, 53.03, 30.09, 15.41.

IR (KBr): 2934, 2854, 1664, 1605, 1540, 1485, 1424, 1403, 1349, 1321, 1266, 1235, 1195, 1153, 1137, 1095, 1051, 1021, 978, 921, 842, 796, 703.

Example 2 trans-1,4-Cyclohexanedicarboxylic acid bis-(N-deacetylthiocolchicine)amide 10 g of N-deacetylthiocolchicine are dissolved in 60 ml of methylene chloride. 2.31 g (0.5 eq) of trans-1,4-cyclohexanedicarboxylic acid, 1.64 g (0.5 eq) of DMAP and 8.3 g (1.5 eq) of DCC are then added with under vigorous stirring. The mixture is left under stirring for 12 hours and monitored by TLC (AcOEt:MeOH 10:1), then filtered through Celite, washing the pad with methylene chloride (2×20 ml). The combined organic phases are washed with an same equal volumes of 1N HCl, 1N NaOH and brine, dried over $Na_2SO_4$. After evaporation of the solvent under reduced pressure, the residue is purified by direct column chromatography (AcOEt: MeOH 12:1). The product is crystallized from methanol (10 v/v) and dried overnight in a static dryer at 40° C. under vacuum to give 6.6 g of pure compound.

$^1$HNMR (300 MHz, $CDCl_3$): 1.30-1.45 (m), 1.45-1.70 (m, 2H), 1.80-1.89 (m), 1.89-2.10 (m), 2.18-2.56 (m), 2.43 (s, 3H, SMe), 3.69 (s, 3H, MeO-1), 3.92 (s, 3H, MeO-2), 3.97 (s, 3H, MeO-3), 4.80-4.92 (m, 2H, H-7), 6.47 (s, 2H, H-8), 7.09 (d, 12.0 Hz, 2H, H-12), 7.34 (d, 12.0 Hz, 2H, H-11), 7.86 (s, 2H, H-4), 8.93 (br s, 2H, NH).

$^{13}$CNMR (75 MHz, $CDCl_3$): 182.44, 176.35, 158.52, 153.80, 152.96, 151.55, 141.97, 139.22, 135.04, 134.69, 129.93, 127.09, 126.37, 107.04, 62.39, 61.68, 56.45, 51.13, 44.59, 36.92, 30.63, 29.61, 27.84, 15.36.

IR (KBr): 3442, 3285, 2934, 2855, 1674, 1602, 1532, 1484, 1454, 1424, 1403, 1390, 1348, 1321, 1281, 1256, 1236, 1195, 1153, 1136, 1094, 1022, 982, 942, 921, 841, 619, 582.

Example 3

3,5-Benzenedicarboxylic acid bis-(N-deacetylthiocolchicine)amide

The procedure of example 1 is followed starting from 5 g of isophtalic acid to obtain the product as a crystalline solid (yield: 82%).

$^1$HNMR (300 MHz, $CDCl_3$): 1.00-1.42 (m, 2H), 1.50-2.00 (m, 2H), 2.05-2.30 (m, 2H), 2.30-2.50 (m, 2H), 2.52 (s, 3H, SMe), 3.71 (s, 3H, MeO-1), 3.90 (s, 3H, MeO-2), 3.96 (s, 3H, MeO-3), 4.80-4.92 (m, 2H, H-7), 6.47 (s, 2H, H-8), 7.18 (d, 12.0 Hz, 2H, H-12), 7.38 (d, 12.0 Hz, 2H, H-11), 7.67 (s, 2H, H-4), 8.52 (br s, 2H, NH), 8.05 (m, 2H, H-4'+H-6'), 8.50 (m, 1H, H-2'), 7.46 (dd, 8.0 Hz, H-5').

Example 4

N-Deacetylthiocolchicine 1,4-phenylenediamine bis-urea 2.0 g of N-deacetylthiocolchicine are dissolved in 150 ml of dry tetrahydrofuran. 0.5 equivalents of 1,4-phenylene diisocyanate (0.4 g) are then added. The reaction mixture is left under stirring at room temperature for two days, monitoring by TLC (DCM-EtOH 95:5, Rf=0.30). The solvent is evaporated off and the crude is recrystallized from ethyl acetate to obtain 0.95 g of pure product (38%).

$^1$HNMR (300 MHz, DMSO-d6): 1.72-1.88 (m), 2.08-2.36 (m), 2.58-2.70 (m), 2.42 (s, 3H, SMe), 3.58 (s, 3H, MeO-1), 3.82 (s, 3H, MeO-2), 3.87 (s, 3H, MeO-3), 4.24-4.35 (m, 2H, H-7), 6.82 (s, 2H, H-8), 7.17 (d, 12.0 Hz, 2H, H-12), 7.27 (d, 12.0 Hz, 2H, H-11), 7.13 (s, 2H, H-4), 8.52 (br s, 2H, NH).

Example 5 n-Deacetylthiocolchicine 1,3-phenylenediamine bis-urea

The procedure of example IV is followed starting from 2.0 g of N-deacetylthiocolchicine and 0.4 g of 1,3-phenylene diisocyanate to obtain the desired product (yield: 42%).

$^1$HNMR (300 MHz, DMSO-d6): 1.72-1.88 (m), 2.08-2.36 (m), 2.58-2.68 (m), 2.43 (s, 3H, SMe), 3.58 (s, 3H, MeO-1), 3.83 (s, 3H, MeO-2), 3.87 (s, 3H, MeO-3), 4.24-4.35 (m, 2H, H-7), 6.82 (s, 2H, H-8), 7.18 (d, 12.0 Hz, 2H, H-12), 7.28 (d, 12.0 Hz, 2H, H-11), 7.14 (s, 2H, H-4), 8.48 (br s, 2H, NH).

Example 6

2,9-Diazasebacic acid bis-(N-deacetylthiocolchicine)amide

The procedure of example IV is followed starting from 2.0 g of N-deacetylthiocolchicine and 0.4 g of 1,4-butanediisocyanate to obtain the desired product (yield: 63%, 0.4 g). TLC (DCM-EtOH=95:5) Rf=0.38.

$^1$HNMR (300 MHz, $CDCl_3$): 1.80-1.95 (m), 2.38-2.54 (m), 2.70-2.95 (m), 3.40-3.60 (m), 2.50 (s, 3H, SMe), 3.69 (s, 3H, MeO-1), 3.95 (s, 3H, MeO-2), 3.98 (s, 3H, MeO-3), 4.54-4.65 (m, 2H, H-7), 6.58 (s, 2H, H-8), 7.21 (d, 12.0 Hz, 2H, H-12), 7.43 (d, 12.0 Hz, 2H, H-11), 7.81 (s, 2H, H-4), 8.20 (br s, 2H, NH).

Example 7

1,3-Benzenemethylene-bis-N-deacetylthiocolchicine 2.0 g of N-deacetylthiocolchicine are dissolved in 100 ml of chloroform. 0.5 Equivalents of isophtalic aldehyde dimethylacetal and 0.01% of pyridinium tosylate are added. The mixture is refluxed overnight, allowed to cool down to room temperature and placed in an ice bath. 8 Equivalents of sodium triacetoxy borohydride are added and the mixture is left under stirring for 1 day. The solution is then filtered, washed with the same volume of 0.1 N HCl and then with saturated aqueous sodium bicarbonate. The organic phase is dried over sodium sulfate and the solvent is evaporated off. The crude is purified by flash chromatography to give 0,49 g of product.

$^1$HNMR (300 MHz, $CDCl_3$): 1.00-1.42 (m, 2H), 1.50-2.00 (m, 2H), 2.05-2.30 (m, 2H), 2.30-2.50 (m, 2H), 2.52 (s, 3H, SMe), 3.71 (s, 3H, MeO-1), 3.90 (s, 3H, MeO-2), 3.96 (s, 3H, MeO-3), 4.80-4.92 (m, 2H, H-7), 6.47 (s, 2H, H-8), 7.18 (d, 12.0 Hz, 2H, H-12), 7.38 (d, 12.0 Hz, 2H, H-11), 7.67 (s, 2H, H-4), 8.52 (br s, 2H, NH), 7.02 (m, 5H).

Example 8

Injectable Formulation of 3,5-pyridinedicarboxylic acid bis-(N-deacetylthiocolchicine)amide Complexed with Human Albumin 1 g of 3,5-pyridinedicarboxylic acid bis-(N-deacetylthiocolchicine)amide is dissolved in 20 ml of dioxane. The result-

The invention claimed is:

1. A compound of formula I

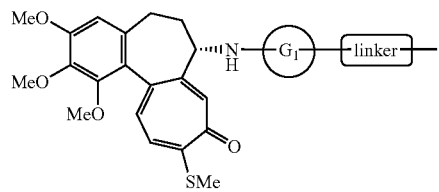

I

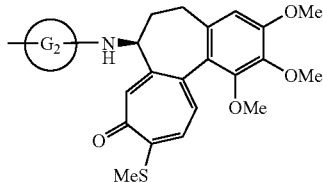

-continued wherein,
the linker is piperazinyl,
the junctions $G_1$ and $G_2$ are both —CO— or —CONH, and
the linker is linked to $G_1$ and $G_2$ through two carbon atoms located at a carbon ring position selected from the group consisting of 3,5 of the ring, 2,5 of the ring, and 2,6 of the ring.

2. A pharmaceutical composition comprising the compound of formula I of claim 1 as an active ingredient in admixture with suitable carriers and/or excipients.

* * * * *